(12) United States Patent
Falotico et al.

(10) Patent No.: US 10,029,034 B2
(45) Date of Patent: Jul. 24, 2018

(54) DRUG-ELUTING ARTICLES WITH IMPROVED DRUG RELEASE PROFILES

(75) Inventors: Robert Falotico, Belle Mead, NJ (US); Jonathon Z. Zhao, Belle Mead, NJ (US)

(73) Assignee: Cardinal Health Switzerland 515 Gmbh, Bar Zug (CH)

(*) Notice: Subject to any disclaimer, the term of this patent is extended or adjusted under 35 U.S.C. 154(b) by 2240 days.

(21) Appl. No.: 11/300,821

(22) Filed: Dec. 15, 2005

(65) Prior Publication Data

US 2007/0141112 A1    Jun. 21, 2007

(51) Int. Cl.
| | |
|---|---|
| A61F 13/00 | (2006.01) |
| A61L 31/16 | (2006.01) |
| A61L 27/34 | (2006.01) |
| A61L 27/54 | (2006.01) |
| A61L 29/08 | (2006.01) |
| A61L 29/16 | (2006.01) |
| A61L 31/10 | (2006.01) |

(52) U.S. Cl.
CPC ............ *A61L 31/16* (2013.01); *A61L 27/34* (2013.01); *A61L 27/54* (2013.01); *A61L 29/085* (2013.01); *A61L 29/16* (2013.01); *A61L 31/10* (2013.01); *A61L 2300/61* (2013.01)

(58) Field of Classification Search
CPC .................................. A61L 2/00; A61L 2/06
USPC ................................................ 424/422–426
See application file for complete search history.

(56) References Cited

U.S. PATENT DOCUMENTS

| | | | | |
|---|---|---|---|---|
| 5,726,167 | A * | 3/1998 | Dodge et al. ................ | 514/172 |
| 5,747,060 | A * | 5/1998 | Sackler ................ | A61K 31/165 |
| | | | | 424/426 |
| 5,824,048 | A | 10/1998 | Tuch | |
| 5,873,904 | A * | 2/1999 | Ragheb et al. .............. | 623/1.13 |
| 2002/0113183 | A1 * | 8/2002 | Mattesky .................. | 248/220.41 |
| 2002/0133183 | A1 * | 9/2002 | Lentz et al. ................... | 606/155 |
| 2003/0004565 | A1 * | 1/2003 | Harnek et al. ............... | 623/1.15 |
| 2003/0096940 | A1 * | 5/2003 | Drumright ............ | C08G 63/08 |
| | | | | 528/196 |
| 2003/0133183 | A1 * | 7/2003 | Yeniay ................. | H01S 3/06754 |
| | | | | 359/349 |
| 2005/0021131 | A1 * | 1/2005 | Venkatraman et al. ..... | 623/1.19 |
| 2005/0058684 | A1 | 3/2005 | Shanley et al. | |
| 2005/0070989 | A1 * | 3/2005 | Lye ........................... | A61F 2/91 |
| | | | | 623/1.4 |
| 2005/0163821 | A1 | 7/2005 | Sung et al. | |
| 2006/0122264 | A1 | 6/2006 | Uchida et al. | |
| 2006/0275341 | A1 * | 12/2006 | Liu ....................... | A61L 31/146 |
| | | | | 424/426 |

FOREIGN PATENT DOCUMENTS

| | | | |
|---|---|---|---|
| EP | 1586337 | A | 10/2005 |
| EP | 1588725 | A | 10/2005 |
| JP | 2003533493 | A | 11/2003 |
| JP | 2005270658 | A | 10/2005 |
| JP | 2005305154 | A | 11/2005 |
| WO | WO 01/87372 | A | 11/2001 |
| WO | WO2004012676 | A2 | 2/2004 |
| WO | 2004026361 | A1 | 4/2004 |
| WO | WO-2004026361 | A1 * | 4/2004 ......... A61K 31/4353 |
| WO | WO 04/108129 | A1 | 12/2004 |
| WO | WO 04/112864 | A | 12/2004 |
| WO | WO 06/116989 | A2 | 11/2006 |

OTHER PUBLICATIONS

Schmidmaier, G., et al. "A New Biodegradable Polylactic Acid Coronary Stent-Coating, Releasing PEG-Hirudin and a Prostacycline Analog, Reduces Both Platelet Activation and Plasmatic Coagulation", Journal of the American College of Cardiology (1997) XP 2068341.

Schmidmaier, G, et al. "Time Release Characteristics of a Biodegradable Stent Coating with Polylactic Acid Releasing PEG-Hirudin and PG12-Analog", Journal of the American College of Cardiology (1997) XP 2323838.

European Search Report dated Jul. 16, 2009 issued on corresponding Application No. 06256316.8-1219.

Examination report for co-pending European Application No. 06256316.8, dated Aug. 21, 2015.

Office Action corresponding to European Application No. 06256316.8; dated May 4, 2017, 7 pages.

* cited by examiner

*Primary Examiner* — Micah Paul Young
(74) *Attorney, Agent, or Firm* — Dergosits & Noah LLP; Todd A. Noah

(57) ABSTRACT

The present invention relates to drug-eluting articles with multiple polymeric coatings arranged and constructed to provide improved drug release profiles. Specifically, the present invention relates to drug-eluting articles that each comprises a substrate, a first polymeric layer over said substrate, and a second polymeric layer over said first polymeric layer. The first polymeric layer comprises at least a first biocompatible polymer and at least a first pharmacologically active compound that is encapsulated in the first biocompatible polymer. The second polymeric layer comprises at least a second biocompatible polymer having a degradability that is higher than that of the first biocompatible polymer.

32 Claims, 2 Drawing Sheets

DRUG-ELUTING ARTICLES WITH IMPROVED DRUG RELEASE PROFILES

FIELD OF THE INVENTION

The present invention relates to drug-eluting articles for controlled local delivery of pharmacologically active agents. More specifically, the present invention relates to drug-eluting articles with multiple polymeric coatings arranged and constructed to provide improved drug release profiles.

BACKGROUND OF THE INVENTION

In recent years, drug-eluting implantable medical devices, such as, for example, stents, stent grafts, anastomosis devices, vascular grafts, vascular patches, AV shunts, catheters, guide wires, balloons, and filters, have gained more and more acceptance in the medical device industry as an effective means for controlled and sustained local drug delivery. Various drug-eluting coating materials can be applied to the surface of traditional implantable medical devices to impart desired pharmacological effects to the otherwise inert devices, in addition to the basic, mechanical functions performed by the traditional, uncoated devices.

Typically, the drug-eluting coatings comprise one or more biocompatible polymers with the desired pharmacologically active agents encapsulated therein. After implantation of such drug-eluting implantable medical devices, the desired pharmacologically active agents (such as, for example, anti-inflammatory and anti-neoplastic agents) are slowly released from the device surfaces into the local environment in a sustained and controlled manner. Such local drug delivery achieved by the drug-eluting implantable medical devices does not result in any significant increase of the overall drug concentration in the body, thereby substantially reducing the potential toxic effects of the drugs commonly associated with systematic administrations (e.g., intravenous, oral or parenteral administrations). Further, the highly localized concentration and prolonged tissue retention of the desired pharmacologically active agents, as achieved by the implanted medical devices, ensure effective treatment of the target diseased site.

However, the drug release profiles of the implantable medical devices, which are defined by the released drug concentrations plotted as a function of time, are typically limited by the physical and chemical properties of the coating materials used, the thickness of the coatings, and the drug concentration in the coatings. Most of the currently available drug-eluting implantable medical devices have sub-optimal drug release profiles. Some of these devices have either too fast a drug release profile, dumping 70% of the drug load within the first day of implantation, or too slow a drug release profile, releasing only about 10% of the drug load after the first half year of implantation. These design flaws significantly undermine the efficacy of such drug-eluting devices.

Moreover, many of the diseases to be treated by the implantable medical devices are multi-faceted, which require the consorted actions of more than one therapeutic agent to achieve optimal and long-standing efficacy. For instance, restenosis, which is the re-narrowing of an artherosclerotic coronary artery after angioplasty or implantation of a bare metal stent, is caused by a cascade of pathological events following the surgery or stent implantation. It is therefore desirable to include a multitude of therapeutic agents in the coatings of the implantable medical devices for treatment of different aspects of restenosis at different stages. Further, it is desirable to include additional therapeutic agents for treatment of certain sub-populations of patients who do not respond favorably to the main therapeutic agent contained in the coatings.

Unfortunately, very few currently available drug-eluting implantable medical devices are specifically designed and configured for delivery of more than one therapeutic agent, much less optimal delivery of multiple therapeutic agents in a time-differentiated manner for treatment of different aspects of a disease at different stages.

Therefore, there is a need for improved drug-eluting articles that have precisely controlled drug release profiles for optimal delivery of one or more therapeutic agents. There is also a need for improved drug-eluting articles that can provide time-differentiated delivery of multiple therapeutic agents, for treatment of different aspects of a disease at different stages.

SUMMARY OF THE INVENTION

The present invention in one aspect relates to a drug-eluting article that comprises:
  a substrate;
  a first polymeric layer over the substrate, wherein the first polymeric layer comprises at least a first biocompatible polymer and at least a first pharmacologically active compound that is encapsulated in the first biocompatible polymer;
  a second polymeric layer over the first polymeric layer, wherein the second polymeric layer comprises at least a second biocompatible polymer having a degradability that is higher than that of the first biocompatible polymer.

The term "polymer" or "polymeric" as used herein refers to any material, composition, structure, or article that comprises one or more polymers, which can be homopolymers, copolymers, or polymer blends.

The term "biocompatible" as used herein refers to any material, composition, structure, or article that have essentially no toxic or injurious impact on the living tissues or living systems which the material, composition, structure, or article is in contact with and produce essentially no immunological response in such living tissues or living systems. More particularly, the material, composition, structure, or article has essentially no adverse impact on the growth and any other desired characteristics of the cells of the living tissues or living systems that are in contact with the material, composition, structure, or article. Generally, the methods for testing the biocompatibility of a material, composition, structure, or article is well known in the art.

The term "degradation" as used herein refers to a gradual resorption of an implanted article, or a coating layer thereon, in a physiological environment over time. The resorption process may take place over a short period of time (e.g., a few hours) or a long period of time (e.g., a few years). The resorption process may occur as a result of hydrolytic breakdown of the materials, or through an enzymatic process, or due to a combination of both as well as other factors. The term "rate of degradation" or "degradability" as used herein refers to the rate at which the resorption of an implanted article, or a coating layer thereon, occurs. For example, higher degradability in the present invention refers to a faster resorption rate, or a shorter period of time that is needed to complete the resorption process.

In a preferred embodiment of the present invention, the second polymeric layer further comprises a second, different pharmacologically active compound as encapsulated in the second biocompatible polymer. Alternatively, the second polymeric layer may also comprise the first pharmacologically active compound, which is encapsulated in the second biocompatible polymer, but preferably at a concentration (measured by weight percentage) that is different from (i.e., either higher or lower than) the concentration of the first pharmacologically active compound in the first polymeric layer.

The drug-eluting article of the present invention may further comprise a third polymeric layer over the second layer. The third polymeric layer comprises at least a third biocompatible polymer having a degradability that is higher than those of the first and second biocompatible polymers of the first and second layers. Preferably, but not necessarily, the third polymeric layer comprises a pharmacologically active compound that is either the same as or different from the pharmacologically active compound(s) contained in the first and/or second layer(s). In the event that the third polymeric layer also comprises the first pharmacologically active compound, it is preferred that the concentration of the first pharmacologically active compound in the third polymeric layer is different from (i.e., either higher or lower than) that in the first polymer layer.

The drug-eluting article of the present invention may comprise one or more additional polymeric layers over the third polymeric layer as described hereinabove. Such additional polymeric layers may or may not comprise a pharmacologically active compound. Further, the pharmacologically active compound(s) contained by such additional polymeric layers, if any, can be either the same as or different from the pharmacologically active compound(s) contained in the first, second and/or third layer(s).

The drug-eluting article of the present invention is preferably, but not necessarily, an implantable medical devices selected from the group consisting of stents, stent grafts, anastomosis devices, vascular grafts, vascular patches, AV shunts, catheters, guide wires, balloons, and filters.

Other aspects, features and advantages of the invention will be more fully apparent from the ensuing disclosure and appended claims.

DETAILED DESCRIPTION OF THE INVENTION, AND PREFERRED EMBODIMENTS THEREOF

Figure 1:
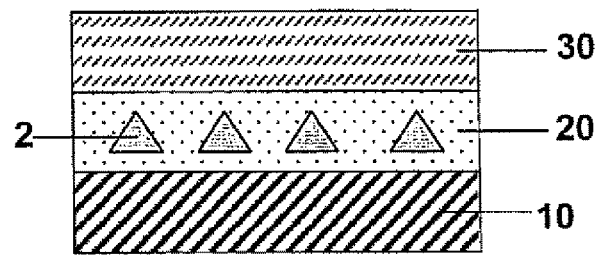
FIGS. 1-3 are partial cross-sectional views of various drug-eluting articles that each contains two polymeric coating layers, according to specific embodiments of the present invention.

In the following description, numerous specific details are set forth, such as particular materials, compositions, formula, structures, devices, and methods for fabricating or using same, in order to provide a thorough understanding of the present invention. However, it will be appreciated by one of ordinary skill in the art that the invention may be practiced without these specific details. In other instances, well-known materials, structures or processing steps have not been described in detail in order to avoid obscuring the invention.

The present invention provides a drug-eluting article that comprises at least one primary polymeric layer and one or more secondary polymeric layers. The primary polymeric layer contains one or more primary pharmacologically active compounds and is coated over a substrate of the drug-eluting article of the present invention for controlled and sustained delivery of the primary pharmacologically active compounds for treatment of a disease. The one or more secondary polymeric layers are formed over the primary drug-containing polymeric layer, for modulating and improving the drug release profile of the drug-eluting article.

The secondary polymeric layers of the drug-eluting article of the present invention may or may not contain any pharmacologically active compounds. However, in several preferred embodiments of the present invention, one or more of the secondary polymeric layers contain one or more secondary pharmacologically active compounds that are different from the primary pharmacologically active compound. In such embodiments, the secondary polymeric layers are used to achieve time-differentiated delivery of multiple therapeutic agents, for treatment of different aspects of a disease at different stages. Alternatively, one or more of the secondary polymeric layers may comprise the primary pharmacologically active compound, preferably at a different concentration. In this manner, the secondary polymeric layers are used for further modifying and adjusting the release profile of the primary pharmacologically active compound.

Both the primary and secondary polymeric layers of the drug-eluting article of the present invention are formed by one or more biocompatible polymers, provided that the biocompatible polymer that forms a relatively outer layer has a higher degradability than the biocompatible polymer that forms a relatively inner layer. In other words, the polymeric coatings of the drug-eluting article of the present invention are characterized by a degradability gradient, wherein the innermost polymeric-coating layer has the lowest degradability, and the outer layers have relatively higher degradability. This degradability gradient ensures that degradation of such polymeric coating layers, if any, initializes from the outermost layer and processes gradually from outside to inside, thereby preventing any premature degradation of the inner layers that may lead to undesired peel-off of the polymeric coatings.

In most practical settings, a higher degradability correlates to a lower molecular weight, a less crystalline and more amorphous structure, given the same polymeric composition. For different polymeric compositions of similar molecular weights and degrees of crystallinity, hydrophobicity also affects the degradability of the polymers. Specifically, a more hydrophobic biostable polymer would have a slower drug release rate, if everything else being equal. A more hydrophobic biodegradable polymer would release drug more slowly and degrades more slowly at the same time.

Therefore, a biocompatible polymer of a higher molecular weight, a higher degree of crystallinity, and/or a higher degree of hydrophobicity is more suitable for forming the innermost layer or the inner layers in the present invention, since the layer(s) formed by such a polymer is more resistant to the same solvent(s) than the outer layer(s) and thereby allows for sequential coating of the outer layer(s).

In one specific embodiment of the present invention, the drug-eluting article comprises a first, inner polymeric layer and a second, outer polymeric layer over the substrate. Both the first and second polymeric layers comprise biocompatible polymers, which can be either biostable or biodegradable, provided that the degradability of the second polymeric layer is higher than that of the first polymeric layer.

For example, both the first and second polymeric layers may comprise biocompatible and biostable polymers, while the second polymeric layer is relatively more stable than the second layer. When both the first and second polymeric layers comprise pharmacologically active compounds (either the same or different), the second polymeric layer is preferably characterized by a faster drug release profile than the first polymeric layer. Such faster drug release profile can be achieved by incorporating the pharmacologically active compound(s) at a higher drug concentration, by using a polymeric composition of lower crystallinity, or by using less hydrophobic polymers.

Alternatively, the first polymeric layer may comprise a biocompatible and biostable polymer, while the second polymeric layer comprises a biocompatible and biodegradable polymer.

Further, the first and second polymeric layers may both comprise biocompatible and biodegradable polymers, while the second polymeric layer is relatively more-degradable than the first layer. For example, the second polymeric layer can be formed by polymer(s) of lower molecular weight or lower crystallinity, or by more hydrophilic polymer(s).

In another specific embodiment of the present invention, the drug-eluting article comprises a first, inner polymeric layer, a second, intermediate polymeric layer, and a third, outer polymeric layer. The first, second and third polymeric layers all comprise biocompatible polymers, which can be either biostable or biodegradable, provided that the degradability of the third polymeric layer is higher than the second layer, and that the degradability of the second polymeric layer is higher than the first layer. For example, both the first and second polymeric layers may comprise biocompatible and biostable polymers, while the third polymeric layer comprises a biocompatible and biodegradable polymer, provided that the first polymeric layer is relatively more stable than the second layer. Alternatively, the first polymeric layer may comprise a biocompatible and biostable polymer, while both the second and third polymeric layers biocompatible and biodegradable polymers, provided that the third polymeric layer is relatively more degradable than the second layer. Further, the first, second, and third polymeric layers may all comprise biostable polymers, or alternatively, the first, second, and third polymeric layers may all comprise biodegradable polymers, provided that the above-described degradability gradient is present in such polymeric layers.

The drug-eluting article of the present invention may further comprise any number of additional polymeric layers. For example, the drug-eluting articles of the present invention may comprise one additional polymeric layer, thereby resulting in a coated structure with four polymeric coatings in total.

Alternatively, the drug-eluting articles of the present invention may comprise two additional polymeric layers, thereby resulting in a coated structure with five polymeric coatings in total.

Any suitable polymer, such as a homopolymer, a copolymer, or a blend of two or more polymers, can be used in the present invention, as long as such a polymer is biocompatible and can be used for forming a polymeric coating layer over a substrate of the drug-eluting articles of the present invention.

Suitable biocompatible and biostable polymers that are suitable for use in the present invention include, but are not limited to: polyurethanes, polyesters, polyolefins such as poly(4-methyl-1-pentene) (PMP), polyethylene (PE), polypropylene (PP), and copolymers of polyethylene and polypropylene (PE/PP), polyamides, poly(esteramide), polycaprolactam, polyimides, polyvinyl chloride, polyvinyl methyl ether, polyvinyl alcohols, acrylic polymers and copolymers, polyacrylonitrile; polystyrene copolymers of vinyl monomers with olefins (such as styrene acrylonitrile copolymers, ethylene methyl methacrylate copolymers, ethylene vinyl acetate), polyethers, elastomers such as butyl rubber, natural rubber, acrylonitrile butadiene styrene (ABS), styrene butadiene styrene (SBS), styrene-isoprene-butadiene-styrene (SIBS), polytetrafluoroethylene (PTFE), expanded PTFE (ePTFE), silicones, rayons, cellulosics (such as cellulose acetate, cellulose nitrate, cellulose propionate, etc.), parylene and derivatives thereof; and mixtures and copolymers of the foregoing.

Suitable biocompatible and biodegradable polymeric materials that can be used in the present invention include, but are not limited to: polylactic acid (PLA), polyglycolid acid (PGA), copolymers of lactic acid and glycolic acid (PLGA), polyethylene glycol (PEG), block copolymers of PEG and PLGA (PEG-PLGA), polycaprolactone, polyphosphoester, polyorthoester, poly(hydroxy butyrate), poly(diaxanone), poly(hydroxy valerate), poly(hydroxy butyrate-co-valerate), poly(glycolide-co-trimethylene carbonate), polyanhydrides, polyphosphoester, poly(ester-amide), polyphosphoeser, polyanhydride, polyphosphazene, poly(phosphoester-urethane), poly(amino acids), polycyanoacrylates, biopolymeric molecules such as fibrin, fibrinogen, cellulose, starch, collagen and hyaluronic acid, and mixtures and copolymers of the foregoing.

Preferably, at least one polymeric coating layer of the present invention comprises a biocompatible and biodegradable polymeric material selected from the group consisting of PLA, PGA, PLGA, and mixtures thereof. More preferably, at least one polymeric coating layer of the present invention comprises the PLGA copolymer. The PLA, PGA, or PLGA polymers may be any of D-, L- and D-/L-configuration. It is preferred that at least one polymeric coating layer of the present invention comprises PLA, PGA, or PLGA polymers with a ratio of D-/L-configuration (mol %) ranging from about 75/25 to about 25/75, more preferably from about 60/40 to about 30/70.

The degradation process of the above-mentioned biodegradable polymers, either in vivo or in vitro, is affected by several factors, including preparation method, molecular weight, composition, chemical structure, size, shape, crystallinity, surface morphology, hydrophobicity, glass transition temperature, site of loading, physicochemical parameters in the surrounding environment (such as pH, temperature, and ionic strength), and mechanism of hydrolysis. For example, the degradation of a biodegradable polymer depends on, inter alia, the hydrophilicity of the polymer: the more hydrophilic the polymer, the more rapid its degradation. The hydrophilicity of the polymer is influenced by the ratio of crystalline to amorphous regions, which in turn is determined by the polymeric composition and monomer stereochemistry. PLGA copolymer prepared from L-PLA and PGA are typically crystalline copolymers, while those prepared from D-, L-PLA and PGA are typically amorphous in nature. Lactic acid, being more hydrophobic than glycolic acid, makes lactic acid-rich PLGA copolymers less hydrophilic and subsequently slows down the degradation process. In general, the degradation time will be shorter for low molecular weight, more hydrophilic, more amorphous biodegradable polymers and copolymers with higher content of glycolic acid. In accordance with these variables, the in vivo degradation of the D-, L-PLGA copolymer may vary from a few weeks to more than 1 year.

In a preferred but not necessary embodiment of the present invention, all the polymeric layers contained by the drug-eluting article of the present invention comprise the same type of biocompatible and biodegradable polymers, while the molecular weight of the polymers contained by any specific polymeric layer is lower than that of the underlying layer. Alternatively, the crystallinity and/or hydrophobicity of the polymers contained by any specific polymeric layer is lower than that of the underlying layer. Because for biodegradable polymers, lower molecular weight, lower hydrophobicity, and/or lower crystallinity correlates with faster degradation rate while other parameters provided the same, forming the outer polymeric layers with biodegradable polymers of lower molecular weight, lower hydrophobicity, and/or lower crystallinity ensures that the outer layers are more degradable than the inner layers.

The specific types and concentrations of the pharmacologically active compounds in the polymeric coating layers of the present invention may vary widely, depending on the specific disease to be treated and the associated treatment requirements.

Preferably, at least one of the pharmacologically active compounds contained by the drug-eluting article of the present invention is a small molecule compound, such as rapamycin, taxane, or estradiol. More preferably, the pharmacologically active compounds are selected from the group consisting of anti-inflammatory compounds, anti-neoplastic compounds, immunosuppressant compounds, anti-restenotic compounds, and anti-thrombotic compounds. Such pharmacologically active compounds may comprise at least one of: rapamycin, rapamycin derivatives such as everolimus, biolimus, zotarolimus (formerly known as ABT-578), pimecrolimus, and tacrolimus, phosphatidylinositol 3 kinase inhibitors (PI3 kinase inhibitor) such as wortmannin and derivatives/analogs thereof (e.g., viridiol, virudin, demethoxyviridin, etc.), taxanes such as paclitaxel, docetaxel, camptothecin, estradiol, Panzem, morphine, epothilone, matrix metalloproteinase (MMP) inhibitor such as tetracycline, and their associated derivatives and analogs. These compounds have anti-inflammatory and anti-neoplastic effects and can therefore be used for preventing and/or treating restenosis-induced vascular diseases, such as restenosis, vulnerable plaque, aneurysm, and/or stroke, post an angioplasty procedure.

In a particularly preferred, but not necessary, embodiment of the present invention, the drug-eluting article of the present invention comprises at least rapamycin or a derivative or analog of rapamycin, such as, for example, everolimus, biolimus, zotarolimus, pimecrolimus, and tacrolimus. Rapamycin, also referred to as sirolimus, is a macrocyclic triene antibiotic produced by Streptomyces hygroscopicus as disclosed in U.S. Pat. No. 3,929,992. It has been found that rapamycin, among other things, inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls. Rapamycin reduces vascular hyperplasia by antagonizing smooth muscle proliferation in response to mitogenic signals that are released during an angioplasty-induced injury. Inhibition of growth factor and cytokine mediated smooth muscle proliferation at the late G1 phase of the cell cycle is believed to be the domain mechanism of action of rapamycin. However, rapamycin is also known to prevent T-cell proliferation and differentiation when administered systematically, and it therefore can be used as an immunosuppressant for preventing graft rejection.

Rapamycin has the following chemical structure:

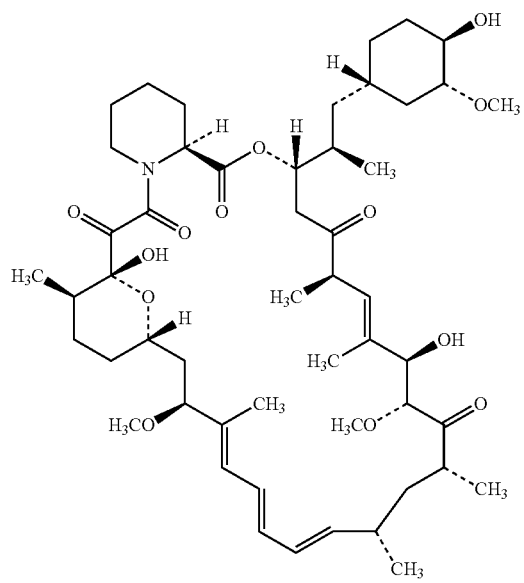

Specifically, a functional domain of the rapamycin molecule that includes the three double bonds is capable of binding to the mammalian target of rapamycin (mTOR), a kinase required for cell-cycle progression. Inhibition of the mTOR kinase activity by rapamycin blocks T-cell activation and proinflammatory cytokine secretion and is the underlying mechanism responsible for the immunosuppressant and anti-hyperplasic activities of rapamycin. Therefore, rapamycin derivatives having similar functional domains are also capable of binding to the mTOR kinase and exhibit immunosuppressant and anti-hyperplasic activities.

In an alternative embodiment of the present invention, the drug-eluting article of the present invention comprises at least one taxane, such as, for example, docetaxel, paclitaxel, or a derivative or analog thereof. The drug-eluting article of the present invention can also comprise other small molecular weight drugs, such as mycophenolate acid (MPA), estradiol, cladribine, probucol, etc.

In addition, large molecular weight entities, such as proteins, oligo-peptides, polypeptides, DNA plasmids, DNAs, RNAs, ribozymes, DNases, siRNAs, anti-sense drugs, etc., can also be readily incorporated into the multi-layer polymeric coating matrix of the drug-eluting articles of the present invention.

The multi-layer polymeric coating matrix contained in the drug-eluting article of the present invention provides more flexibility in selecting an appropriate polymeric material for carrying and sustaining a specific pharmacologically active compound. First, the selected polymeric material should have similar hydrophobicity or hydrophilicity with the active compound, in order to achieve satisfactory homogeneity between the active compound and the polymeric coating matrix, which in turn improve the stability and drug release kinetics of the polymeric coating matrix. For example, a pharmacologically active compound that is hydrophobic can be readily encapsulated into a hydrophobic polymeric matrix to form a stable suspension or even a true solid solution of such a pharmacologically active compound. On the other hand, a hydrophilic or water-soluble compound can be readily encapsulated into a hydrophilic polymeric matrix to form a similarly stable mixture. Second, it is important that the selected polymeric material does not interact with the active compound in any manner that would interfere with the pharmacological functionality of the active compound.

The multi-layer polymeric coating matrix contained in the drug-eluting article of the present invention also provides an effective means for physically separating two or more pharmacologically active compounds that may interact with each other in an adverse manner. Specifically, the compounds that may adversely interact with each other are separately incorporated into different polymeric coating layers, thereby reducing the interactions therebetween. Further, a thin layer of polymeric coating material that does not contain any active compounds can be provided between those polymeric layers that separately contain adversely interacting compounds, so as to ensure maximum separation.

The multi-layer polymeric coating matrix of the present invention further provides a means for achieving time-differentiated delivery of multiple pharmacologically active compounds. For example, those pharmacologically active compounds that can be used for treatment of certain aspects of a target disease at earlier stages can be incorporated into outer polymeric layers for early-stage delivery. On the other hand, those pharmacologically active compounds that can be used for treatment of other aspects of the target disease at later stages can be incorporated into inner polymeric layers for late-stage delivery.

Further, each polymeric layer in the polymeric coating matrix of the present invention may comprise two or more pharmacologically active compounds at various concentrations, so that the delivery profiles of two or more pharmacologically active compounds can be independently adjusted in a time-controlled manner, by changing the concentrations of such pharmacologically active compounds in respective polymeric layers. For example, an outer polymeric layer may contain a first pharmacologically active compound at a relatively high concentration and a second pharmacologically active compound at a relatively low concentration, while an inner polymeric layer contains the first pharmacologically active compound at a relatively low concentration and the second pharmacologically active compound at a relatively high concentration. Therefore, the release profile of the first pharmacologically active compound is characterized by a high initial concentration, followed by a prolonged low concentration. In contrast, the release profile of the second pharmacologically active compound is characterized by a low initial concentration, followed by a prolonged high concentration.

More importantly, by incorporating the pharmacologically active compounds into one or more of the inner polymeric layers, higher concentrations of such active compounds can be incorporated, without causing any potentially adverse dose dumping or any burst release immediately after implantation.

The multi-layer polymeric coating matrix in the present invention may further comprise various chelating agents, excipients, and additives that are well known in the art, in order to achieve optimal formulation of the pharmacologically active compounds. These chelating agents, excipients, and additives are particularly desirable for therapeutic agents of relatively large molecular weight, such as proteins, RNAs, DNAs, etc.

The multi-layer polymeric coating matrix of the present invention can be readily formed by any suitable coating method well known in the art. For example, any of the polymeric layers in the coating matrix can be formed by spray-drying a polymer solution, which contains a biocompatible polymer and optionally a pharmacologically active compound dissolved in one or more solvents, onto a previously applied coating layer. Alternatively, any of the polymeric layers can be formed by dipping the previously coated article into a polymer solution, followed by drying. Other methods for applying polymeric materials to substrates, such as extrusion, spin coating, in situ polymerization, etc., can also be used to form such polymeric layers.

Priming layer can be applied onto the substrate before application of the first polymeric layer. Adhesion promotion materials can also be applied onto a previously applied coating layer coating before coating of the next layer. The priming layer and the adhesion promotion materials function to improve the adhesion between the coating layers and the substrate and to prevent peel-off of any coating layers.

Further, a previously applied coating layer can be treated by various methods, such as, for example, thermal annealing, pressure annealing, vacuuming, and/or cross-linking, before coating of the next layer. Such treatment functions to further improve the stability and drug release kinetics of the polymeric coating matrix.

The following examples are provided hereinafter to illustrate various exemplary drug-eluting articles with multi-layer polymeric coating matrices, according to preferred embodiments of the present invention:

EXAMPLE 1

FIG. 1 shows a partial cross-sectiorial view of a drug-eluting article with two polymeric coating layers, according to one embodiment of the present invention. Specifically, the drug-eluting article contains a substrate 10, over which two polymeric layers 20 and 30 are formed. The inner polymeric layer 20 comprises a first biocompatible polymer, while a first pharmacologically active compound 2 is encapsulated in the first biocompatible polymer. The outer polymeric layer 30 comprises a second biocompatible polymer, and is essentially free of any pharmacologically active compound.

The first and second biocompatible polymers may be the same type of polymers, or they can be different, provided that the second biocompatible polymer has a higher degradability than the first polymer. For example, the first biocompatible polymer can be biostable, while the second polymer is biodegradable. Alternatively, both the first and second biocompatible polymers can be biodegradable, provided that the molecular weight of the second polymer is lower than that of the first polymer, in order to ensure higher degradability of the second polymer.

EXAMPLE 2

Figure 2:
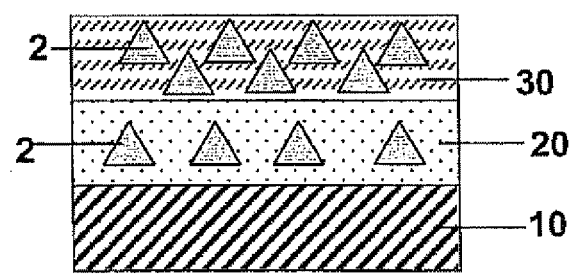

FIG. 2 shows a partial cross-sectional view of a drug-eluting article, which is the same as that shown by FIG. 1, except that the second polymeric layer 30 in FIG. 2 also contains the pharmacologically active compound 2, but at a higher concentration than the first polymeric layer 20. Alternatively, the second polymeric layer 30 may contain the pharmacologically active compound 2 at a lower concentration than the first polymeric layer 20.

EXAMPLE 3

Figure 3:
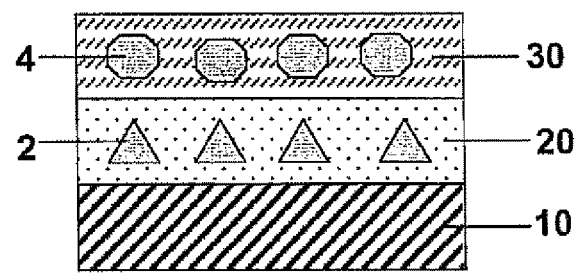

FIG. 3 shows a partial cross-sectional view of a drug-eluting article, which is the same as that shown by FIG. 1, except that the second polymeric layer 30 in FIG. 2 contains a pharmacologically active compound 4, which is different from the pharmacologically active compound 2. Preferably, but not necessarily, the first pharmacologically active compound 2 is an anti-restenotic compound, and the second pharmacologically active compound 4 is an anti-thrombotic or anti-inflammatory compound.

Further, the first and second polymeric layers 20 and 30 may both contain the pharmacologically active compounds 2 and 4, but at different concentrations. In this manner, the release profiles of the pharmacologically active compounds 2 and 4 can be independently adjusted to achieve optimal delivery of both compounds in a time-dependent manner.

EXAMPLE 4

Figure 4:
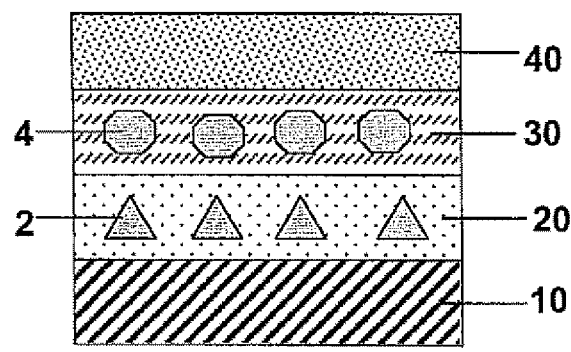
FIGS. 4-6 are partial cross-sectional view of various drug-eluting articles that each contains three polymeric coating layers, according to specific embodiments of the present invention.

FIG. 4 shows a partial cross-sectional view of a drug-eluting article, which is the same as that shown by FIG. 3, except that it contains a third polymeric layer 40 over the second polymeric layer 30. Specifically, the third polymeric layer 40 comprises a third biocompatible polymer, and it is essentially free of any pharmacologically active compound.

The third polymeric layer 40 may comprise the same type of biocompatible polymers as those contained by layers 20 and 30, or it may comprise a different type of polymer, provided that the third biocompatible polymer has a higher degradability than the second polymer contained by layer 30. For example, the first biocompatible polymer can be biodegradable, while both the first and second polymers are biostable. Alternatively, both the second and third biocompatible polymers can be biodegradable, while the first polymer is biostable, provided that the molecular weight of the third polymer is lower than that of the second polymer, thereby ensuring higher degradability of the third polymer. Further, the first, second, and third polymers can all be biodegradable, while the molecular weight of the third polymer is lower than that of the second polymer and the molecular weight of the second polymer is in turn lower than that of the first polymer.

EXAMPLE 5

Figure 5:
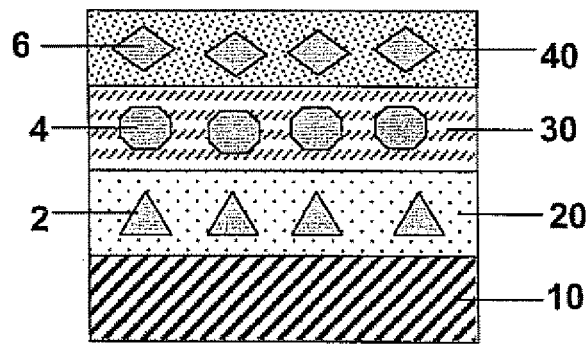

FIG. 5 shows a partial cross-sectional view of a drug-eluting article, which is the same as that shown by FIG. 4, except that the third polymeric layer 40 shown in FIG. 5 contains a pharmacologically active compound 6, which is different from the first and second pharmacologically active compounds 2 and 4.

EXAMPLE 6

Figure 6:
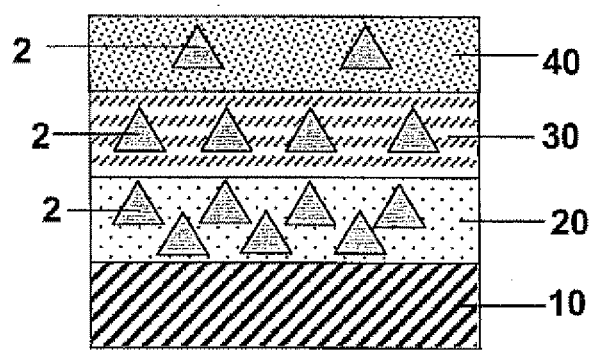

FIG. 6 shows a partial cross-sectional view of a drug-eluting article, which is the same as that shown by FIG. 5, except that the first, second, and third polymeric layers 20, 30, and 40 shown in FIG. 6 all contain the same pharmacologically active compound 2, but at different concentrations. Specifically, the first polymeric layer 20 contains compound 2 at the highest concentration; the second polymeric layer 30 contains compound 2 at an intermediate concentration; and the third polymeric layer 40 contains compound 2 at the lowest concentration. The drug-eluting article as shown in FIG. 6 thereby provides a release profile for compound 2, which is characterized by a gradually increased release concentration over time.

While specific embodiments of the present invention are described and illustrated hereinabove, it is clear that a person ordinarily skilled in the art can readily modify such specific embodiments consistent with the descriptions provided herein. It should therefore be recognized that the present invention is not limited to the specific embodiments illustrated hereinabove, but rather extends in utility to any other modification, variation, application, and embodiment, and accordingly all such other modifications, variations, applications, and embodiments are to be regarded as being within the spirit and scope of the invention.

What is claimed is:

1. A drug-eluting article, comprising:
   a metallic substrate;
   a first polymeric layer over said substrate, wherein said first polymeric layer comprises at least a first biocompatible polymer and at least a first pharmacologically active compound that is encapsulated in the first biocompatible polymer;
   a second polymeric layer over said first polymeric layer, wherein said second polymeric layer comprises at least a second biocompatible polymer having a rate of degradation that is higher than that of the first biocompatible polymer, wherein at least one of the first and second biocompatible polymers comprises PLGA with a D/L ratio ranging from about 60/40 to about 30/70, and wherein the higher rate of degradation of the second polymeric layer as compared to the rate of degradation of the first polymeric layer is a function of at least one of i) higher crystallinity of the second polymeric layer; and ii) higher hydrophilicity of the second polymeric layer.

2. The drug-eluting article of claim 1, wherein the first biocompatible polymer is biostable, and wherein the second biocompatible polymer is biodegradable.

3. The drug-eluting article of claim 1, wherein the first and second biocompatible polymers are both biodegradable, and wherein the second biocompatible polymer has a lower molecular weight than the first biocompatible polymer.

4. The drug-eluting article of claim 1, wherein the first and second biocompatible polymers are both biodegradable, and wherein the second biocompatible polymer is more hydrophilic than the first biocompatible polymer.

5. The drug-eluting article of claim 1, wherein the first and second biocompatible polymers are both biodegradable, and wherein the second biocompatible polymer has a lower crystallinity than the first biocompatible polymer.

6. The drug-eluting article of claim 1, wherein the first and second biocompatible polymers are both biostable, wherein the second biocompatible polymer encapsulates a pharmacologically active compound that is either the same as or different from the first pharmacologically active compound, and wherein the second biocompatible polymer has a faster drug release profile than the first compatible polymer.

7. The drug-eluting article of claim 6, wherein the pharmacologically active compound is present in the second biocompatible polymer at a higher concentration than that of the first pharmacologically active compound in the first biocompatible polymer.

8. The drug-eluting article of claim 6, wherein the second biocompatible polymer has a lower crystallinity than the first biocompatible polymer.

9. The drug-eluting article of claim 6, wherein the second biocompatible polymer is less hydrophobic than the first biocompatible polymer.

10. The drug-eluting article of claim 1, wherein the second polymeric layer further comprises a second, different pharmacologically active compound that is encapsulated in the second biocompatible polymer.

11. The drug-eluting article of claim 1, wherein the second polymeric layer also comprises the first pharmacologically active compound, which is encapsulated in the second biocompatible polymer, and wherein said first pharmacologically active compound presents in the second polymeric layer at a concentration that is different from the concentration of said first pharmacologically active compound in the first polymeric layer.

12. The drug-eluting article of claim 11, wherein the first pharmacologically active compound presents in the second polymeric layer at a concentration that is higher than the concentration of said first pharmacologically active compound in the first polymeric layer.

13. The drug-eluting article of claim 11, wherein the first pharmacologically active compound presents in the second polymeric layer at a concentration that is lower than the concentration of said first pharmacologically active compound in the first polymeric layer.

14. The drug-eluting article of claim 1, wherein the first pharmacologically active compound is selected from the group consisting of anti-inflammatory compounds, anti-neoplastic compounds, immunosuppressant compounds, anti-restenotic compounds, and anti-thrombotic compounds.

15. The drug-eluting article of claim 14, wherein the first pharmacologically active compound is rapamycin or a derivative or analog of rapamycin.

16. The drug-eluting article of claim 15, wherein the first pharmacologically active compound is a derivative or analog of rapamycin selected from the group consisting of everolimus, biolimus, zotarolimus, pimecrolimus, and tacrolimus.

17. The drug-eluting article of claim 14, wherein the first pharmacologically active compound is a phosphatidylinositol 3 kinase inhibitor (PI3 kinase inhibitor).

18. The drug-eluting article of claim 17, wherein the PI3 kinase inhibitor is wortmannin or a derivative or analog of wortmannin selected from the group consisting of viridiol, virudin, demethoxyviridin.

19. The drug-eluting article of claim 14, wherein the first pharmacologically active compound is a taxane selected from the group consisting of docetaxel, paclitaxel, or a derivative or analog thereof.

20. The drug-eluting article of claim 1, wherein the first pharmacologically active compound is a large molecular-weight biologically active entity selected from the group consisting of proteins, oligo-peptides, polypeptides, DNAs, RNAs, DNA plasmids, siRNAs, and an anti-sense molecules.

21. The drug-eluting article of claim 10, wherein the second pharmacologically active compound is selected from the group consisting of anti-inflammatory compounds, anti-neoplastic compounds, immunosuppressant compounds, anti-restenotic compounds, and anti-thrombotic compounds.

22. The drug-eluting article of claim 10, wherein the first pharmacologically active compound is an anti-restenotic compound, and wherein the second pharmacologically active compound is an anti-thrombotic or an anti-inflammatory compound.

23. The drug-eluting article of claim 1, further comprising a third polymeric layer over said second polymeric layer, wherein said third polymeric layer comprises at least a third biocompatible polymer having a degradability that is higher than those of the first and second biocompatible polymers.

24. The drug-eluting article of claim 23, wherein the third polymeric layer comprises a pharmacologically active compound that is either the same as or different from the pharmacologically active compound(s) contained in the first and/or second polymeric layer(s).

25. The drug-eluting article of claim 24, wherein the third polymeric layer also comprises the first pharmacologically active compound, which is encapsulated in the third biocompatible polymer, and wherein said first pharmacologically active compound presents in the third polymeric layer at a concentration that is different from the concentration of said first pharmacologically active compound in the first polymeric layer.

26. The drug-eluting article of claim 23, wherein the first, second, and third biocompatible polymers are all biodegradable.

27. The drug-eluting article of claim 23, wherein the first biocompatible polymer is biostable, and wherein the second and third biocompatible polymers are both biodegradable.

28. The drug-eluting article of claim 23, wherein the first and second biocompatible polymers are both biostable, and wherein the third biocompatible polymer is biodegradable.

29. The drug-eluting article of claim 23, wherein the first, second, and third biocompatible polymers are all biostable.

30. The drug-eluting article of claim 23, further comprising one or more additional polymeric layers over said third polymeric layer.

31. The drug-eluting article of claim 30, wherein at least one of the additional polymeric layers comprise a pharmacologically active compound that is either the same as or different from the pharmacologically active compound(s) contained in the first, second and/or third polymeric layer(s).

32. The drug-eluting article of claim 1, comprising an implantable medical device selected from the group consisting of stents, stent grafts, anastomosis devices, vascular grafts, vascular patches, AV shunts, catheters, guide wires, balloons, and filters.

* * * * *